United States Patent
Nelson et al.

(10) Patent No.: US 7,474,395 B2
(45) Date of Patent: Jan. 6, 2009

(54) SYSTEM AND METHOD FOR IMAGE RECONSTRUCTION IN A FIBER ARRAY SPECTRAL TRANSLATOR SYSTEM

(75) Inventors: Matthew P. Nelson, Harrison City, PA (US); Jason H. Neiss, Pittsburgh, PA (US); Patrick J. Treado, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 176 days.

(21) Appl. No.: 11/674,552

(22) Filed: Feb. 13, 2007

(65) Prior Publication Data

US 2007/0188747 A1    Aug. 16, 2007

Related U.S. Application Data

(60) Provisional application No. 60/772,624, filed on Feb. 13, 2006.

(51) Int. Cl.
*G01J 3/00* (2006.01)
(52) U.S. Cl. .................................... 356/300; 250/252.1
(58) Field of Classification Search ................. 356/300; 250/252.1; 348/167; 702/189
See application file for complete search history.

(56) References Cited

U.S. PATENT DOCUMENTS

| | | | | |
|---|---|---|---|---|
| 5,157,506 A * | 10/1992 | Hannah | | 382/167 |
| 6,219,446 B1 * | 4/2001 | Kiriki et al. | | 382/167 |
| 2004/0037468 A1 * | 2/2004 | Morishima et al. | | 382/218 |
| 2004/0152992 A1 * | 8/2004 | Zeng | | 600/476 |
| 2005/0057676 A1 * | 3/2005 | Weiner et al. | | 348/331 |
| 2008/0192246 A1 * | 8/2008 | Neiss et al. | | 356/301 |
| 2008/0197287 A1 * | 8/2008 | Nelson et al. | | 250/362 |

* cited by examiner

*Primary Examiner*—Kara E Geisel
(74) *Attorney, Agent, or Firm*—Duane Morris LLP

(57) ABSTRACT

The disclosure relates generally to methods and apparatus for spectral calibration of a spectroscopic system which includes a fiber array spectral translator. One embodiment relates to a method for obtaining a first image of a known substance using a photon detector and a fiber array spectral translator having plural fibers, wherein the first image comprises at least one pixel; providing a second image of the substance wherein the second image comprises at least one pixel; comparing the first image with the second image; and adjusting at least one pixel of the first image based on the comparison of images to thereby obtain an adjusted image.

33 Claims, 15 Drawing Sheets

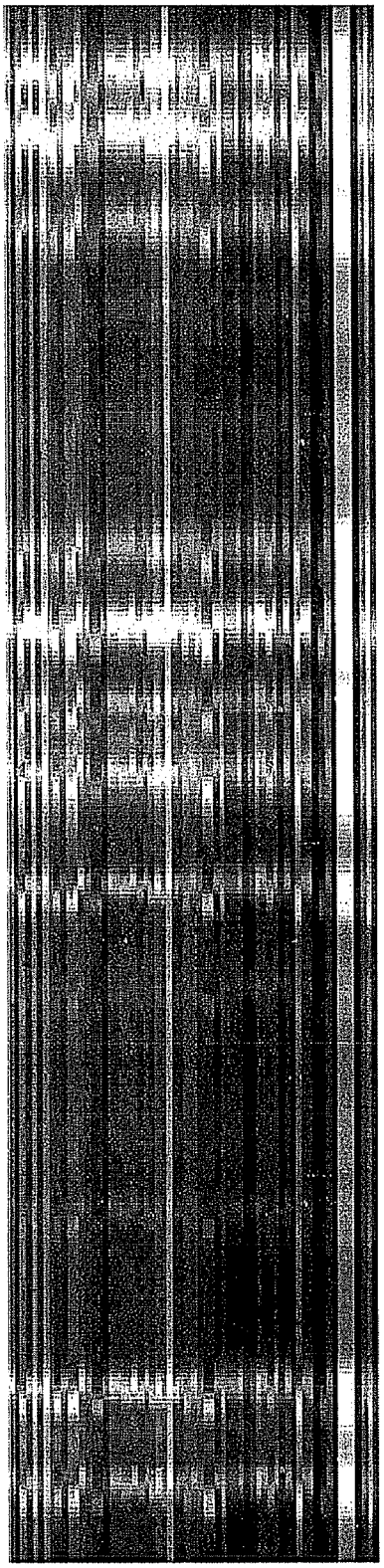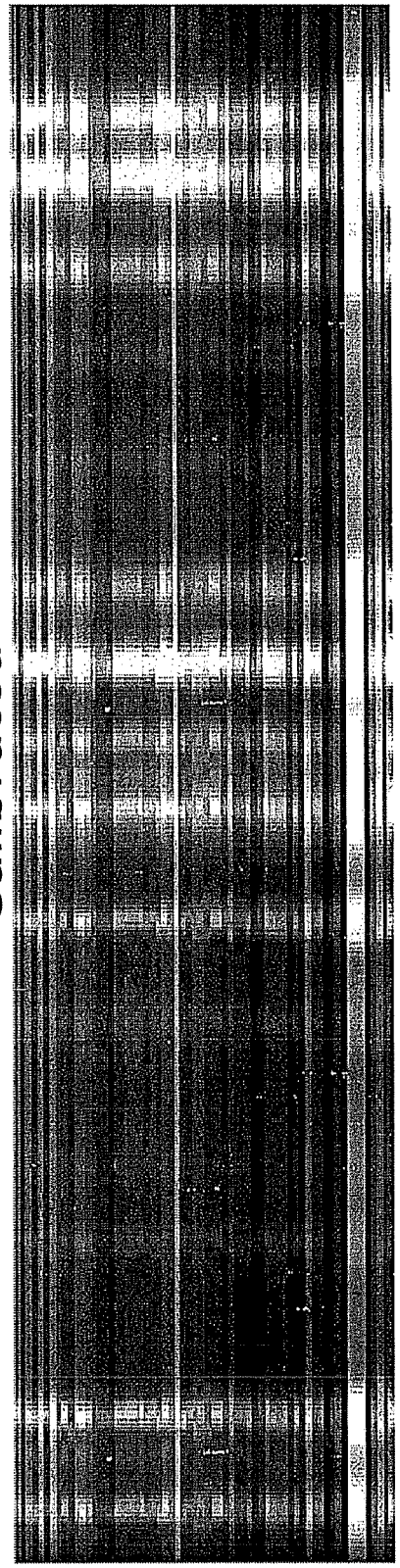
FIGURE 11

SYSTEM AND METHOD FOR IMAGE RECONSTRUCTION IN A FIBER ARRAY SPECTRAL TRANSLATOR SYSTEM

PRIORITY INFORMATION

The instant disclosure claims the filing-date benefit of Provisional Application No. 60/772,624 filed 13 Feb. 2006, entitled "Image Reconstruction in a Fiber Array Spectral Translator (FAST) System", the disclosure of which is incorporated herein in its entirety.

RELATED APPLICATION

The current application is being filed concurrently with U.S. patent application Ser. No. 11/675,155 entitled "System and Method for Super Resolution of a Sample in a Fiber Array Spectral Translator System", the disclosure of which is incorporated herein in its entirety.

BACKGROUND

A fiber array spectral translator ("FAST") system when used in conjunction with a photon detector allows massively parallel acquisition of full-spectral images. A FAST system can provide rapid real-time analysis for quick detection, classification, identification, and visualization of the sample. The FAST technology can acquire a few to thousands of full spectral range, spatially resolved spectra simultaneously. A typical FAST array contains multiple optical fibers that may be arranged in a two-dimensional array on one end and a one dimensional (i.e., linear) array on the other end. The linear array is useful for interfacing with a photon detector, such as a charge-coupled device ("CCD"). The two-dimensional array end of the FAST is typically positioned to receive photons from a sample. The photons from the sample may be, for example, emitted by the sample, reflected off of the sample, refracted by the sample, fluoresce from the sample, or scattered by the sample. The scattered photons may be Raman photons.

In a FAST spectrographic system, photons incident to the two-dimensional end of the FAST may be focused so that a spectroscopic image of the sample is conveyed onto the two-dimensional array of optical fibers. The two-dimensional array of optical fibers may be drawn into a one-dimensional distal array with, for example, serpentine ordering. The one-dimensional fiber stack may be operatively coupled to an imaging spectrograph of a photon detector, such as a charge-coupled device so as to apply the photons received at the two-dimensional end of the FAST to the detector rows of the photon detector.

One advantage of this type of apparatus over other spectroscopic apparatus is speed of analysis. A complete spectroscopic imaging data set can be acquired in the amount of time it takes to generate a single spectrum from a given material. Additionally, the FAST can be implemented with multiple detectors. The FAST system allows for massively parallel acquisition of full-spectral images. A FAST fiber bundle may feed optical information from its two-dimensional non-linear imaging end (which can be in any non-linear configuration, e.g., circular, square, rectangular, etc.) to its one-dimensional linear distal end input into the photon detector.

A problem exists with the prior art's use of a FAST system. The linear array end of the FAST, when input into a photon detector, may become slightly misaligned so that an image produced may be shifted due to the misalignment. Furthermore, the peaks in a spectrum of the sample may not be aligned with the peaks of a known calibrated sample of the same substance and therefore the received peaks may not be calibrated. Additionally, the fibers in the FAST may not allow for a resolution of the resulting image to a degree necessary. The present disclosure, as described herein below, presents methods and systems for overcoming these deficiencies in the prior art.

The combination of calibration and reconstruction methods according to one embodiment of the present disclosure may be useful among fiber optics imaging manufacturers. The calibration and image reconstruction approaches discussed herein are independent of any specific FAST-based imaging applications. Accordingly, it is an object of the present disclosure to provide a method for spectral calibration, comprising obtaining a first image of a known substance using a photon detector and a fiber array spectral translator having plural fibers, wherein said first image comprises at least one pixel; providing a second image of said substance wherein said second image comprises at least one pixel; comparing said first image with said second image; and adjusting at least one pixel of said first image based on said comparison of images to thereby obtain an adjusted image. It is another object of the present disclosure to additionally obtain a first spectrum of said substance from one of said plural fibers wherein said first spectrum comprises at least one peak; provide a second spectrum of said substance wherein said second spectrum comprises at least one peak; compare at least one peak of said first spectrum to at least one peak of said second spectrum; and adjust said first spectrum based on said comparison of peaks.

It is yet another object of the present disclosure to provide a method for spectral calibration, comprising: obtaining a first data set representative of a first image of a known substance, wherein said first data set is obtained using a photon detector and a fiber array spectral translator having plural fibers; providing a second data set representative of a second image of said substance; comparing said first data set with said second data set; and adjusting said first data set based on said comparison of said first and second data sets. It is still another object of the present disclosure to additionally obtain a third data set representative of a first spectrum of said substance from one of said plural fibers wherein said first spectrum comprises at least one peak; provide a fourth data set representative of a second spectrum of said substance wherein said second spectrum comprises at least one peak; compare a part of said third data set representative of at least one peak of said first spectrum to a part of said fourth data set representative of at least one peak of said second spectrum; and adjust said first data set based on said comparison of said third and fourth data sets.

It is a further object of the present disclosure to provide a method for spectral calibration comprising: obtaining a first image of a known substance using a photon detector and a fiber array spectral translator having plural fibers, wherein said first image comprises at least one pixel; providing a second image of said substance wherein said second image comprises at least one pixel; obtaining a first spectrum of said substance from one of said plural fibers wherein said first spectrum comprises at least one peak; providing a second spectrum of said substance wherein said second spectrum comprises at least one peak; comparing said first image with said second image to thereby obtain a bulk shift adjustment; and comparing at least one peak of said first spectrum to at least one peak of said second spectrum to thereby obtain a subpixel adjustment.

It is yet a further object of the present disclosure to provide a method for spectral calibration, comprising: obtaining a first data set representative of a first image of a known substance using a photon detector and a fiber array spectral translator having plural fibers, wherein said first image comprises at least one pixel; providing a second data set representative of a second image of said substance, wherein said second image comprises at least one pixel; obtaining a third data set representative of a first spectrum of said substance from one of said plural fibers wherein said first spectrum comprises at least one peak; providing a fourth data set representative of a second spectrum of said substance wherein said second spectrum comprises at least one peak; comparing said first data set with said second data set to thereby obtain a bulk shift adjustment; and comparing said third data set with said fourth data set to thereby obtain a subpixel adjustment.

It is still a further object of the present disclosure to provide a system for spectral calibration of a known substance, comprising: a photon source for illuminating said substance with first photons to thereby produce second photons; a fiber array spectral translator having plural fibers, wherein said fiber array spectral translator receives said second photons; a photon detector operatively connected to said fiber array spectral translator, wherein said photon detector detects said second photons; a memory unit comprising a first data set representative of a first image of said substance; and a microprocessor unit operatively connected to said photon detector and said memory unit, wherein said microprocessor obtains a second data set from said second photons, compares said first and second data sets, and adjusts said first data set based on said comparison. It is yet still a further object of the present disclosure to further provide a display device operatively connected to said microprocessor unit so as to display an image selected from the group consisting of: said first image, a second image representative of said second data set, an adjusted image representative of said adjusted first data set, and combinations thereof.

BRIEF DESCRIPTION OF THE DRAWINGS

FIG. 11 is a representation of a raw image and a calibrated image of the output of a detector according to an embodiment of the disclosure.

DETAILED DESCRIPTION

The present disclosure relates to spectroscopic systems, particularly fiber arrays spectral translator ("FAST") spectroscopic systems, and more particularly to systems and method for overcoming the alignment and calibration issues present in the prior art. FAST technology can acquire a few to thousands of full spectral range, spatially resolved spectra simultaneously. This may be done by focusing a spectroscopic image onto a two-dimensional array of optical fibers that are drawn into a one-dimensional distal array with, for example, serpentine ordering. The one-dimensional fiber stack is coupled to an imaging spectrograph. A microprocessor and/or software may be used to extract spectral/spatial information that is embedded in a single charge-coupled device ("CCD") image frame.

One of the fundamental advantages of this method over other spectroscopic methods is speed of analysis. A complete spectroscopic imaging data set can be acquired in the amount of time it takes to generate a single spectrum from a given material. FAST can be implemented with multiple detectors. Color-coded FAST spectroscopic images can be superimposed on other high-spatial resolution gray-scale images to provide significant insight into the morphology and chemistry of the sample.

The FAST system allows for massively parallel acquisition of full-spectral images. A FAST fiber bundle may feed optical information from its two-dimensional non-linear imaging end (which can be in any non-linear configuration, e.g., circular, square, rectangular, etc.) to its one-dimensional linear distal end. The distal end feeds the optical information into associated detector rows. The detector may be a CCD detector having a fixed number of rows with each row having a predetermined number of pixels. For example, in a 1024-width square detector, there will be 1024 pixels (related to, for example, 1024 spectral wavelengths) per each of the 1024 rows.

Figure 1:
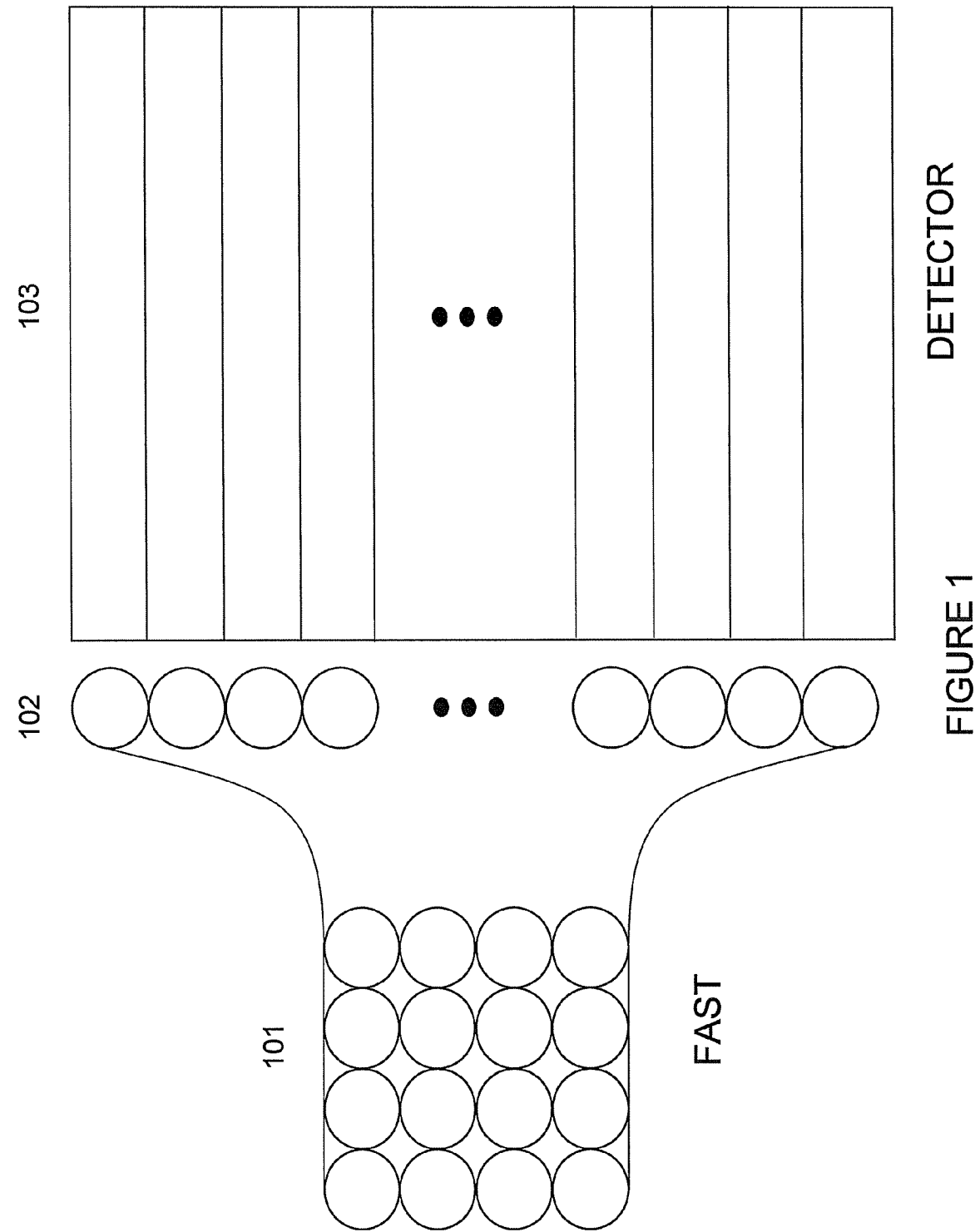
FIG. 1 is a schematic drawing of a fiber array spectral translator.

The construction of the FAST array requires knowledge of the position of each fiber at both the imaging end and the distal end of the array as shown, for example, in the simplified diagram for FIG. 1 where a total of sixteen fibers are shown numbered in correspondence between the imaging end 101 and the distal end 102 of the fiber bundle. As shown in FIG. 1, a FAST fiber bundle may feed optical information from its 2D non-linear imaging end 101 (which can be in any non-linear configuration, e.g., circular, square, rectangular, etc.) to its 2D linear distal end 102, which feeds the optical information into associated detector rows 103. The distal end may be positioned at the input to a photon detector 103, such as a CCD, a complementary metal oxide semiconductor ("CMOS") detector, or a focal plane array sensor (such as InGaAs, InSb, metal oxide semiconductor controlled thyristor ("MCT"), etc.). Photons exiting the distal end fibers may be collected by the various detector rows. Each fiber collects light from a fixed position in the two-dimensional array (imaging end) and transmits this light onto a fixed position on the detector (through that fiber's distal end).

Figure 2:
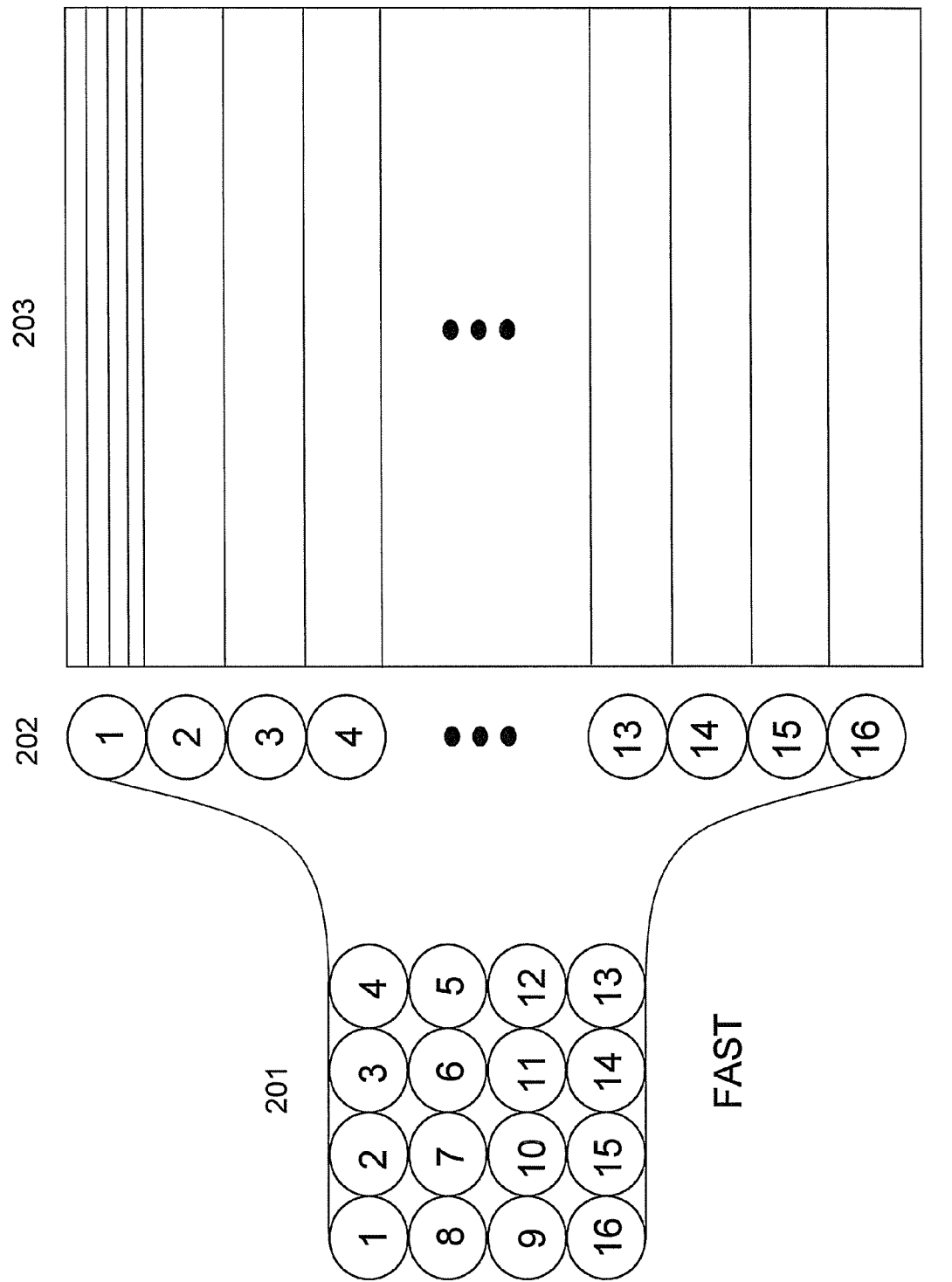
FIG. 2 is a is a schematic drawing of a fiber array spectral translator showing an exemplary spatial mapping arrangement.

FIG. 2 shows a non-limiting exemplary spatial arrangement of fibers at the imaging end 201 and the distal end 202. Additionally, as shown in FIG. 2, each fiber may span more than one detector row in detector 203, allowing higher resolution than one pixel per fiber in the reconstructed image. In fact, this super-resolution, combined with interpolation between fiber pixels (i.e., pixels in the detector associated with the respective fiber), achieves much higher spatial resolution than is otherwise possible. Thus, spatial calibration may involve not only the knowledge of fiber geometry (i.e., fiber correspondence) at the imaging end and the distal end, but also the knowledge of which detector rows are associated with a given fiber.

The calibration of a FAST spectroscopic system may involve spatial calibration and spectral calibration. The construction of the FAST array requires knowledge of the position of each fiber at both the imaging end and the distal end of the array as shown, for example, in the simplified diagram of FIG. 2 where a total of sixteen (16) fibers are shown numbered in correspondence between the imaging end and the distal end of the fiber bundle. Each fiber collects light from a fixed position in the 2D array 201 (imaging end) and transmits this light onto a fixed position on the detector 203 (through that fiber's distal end 202). It shall be understood by those of skill in the art that the number, arrangement, and numbering of the fibers in FIG. 2 is exemplary only and should in no way be construed to limit the current disclosure.

As shown in FIG. 2, each fiber may span more than one detector row, allowing higher resolution than one pixel per fiber in the reconstructed image. In fact, this super-resolution, combined with interpolation between fiber pixels (i.e., pixels in the detector associated with the respective fiber), achieves much higher spatial resolution than is otherwise possible. Thus, spatial calibration may involve not only the knowledge of fiber geometry (i.e., fiber correspondence) at the imaging end and the distal end, but also the knowledge of which detector rows are associated with a given fiber.

The existence of multiple fibers in the FAST requires that each fiber be independently spectrally calibrated. In practice, a miscalibration may manifest itself as each fiber producing spectra with bulk spectral shifts (i.e., a spectral shift of one or more pixels) relative to a standard sample such as acetaminophen. Thus, even though a fiber may be hardware-wise "linked" or "calibrated" to a group of detector rows (for example, as part of a spatial calibration exercise), the spectral calibration may still be performed with a microprocessor and/or in software to "align" the optical spectra among the rows associated with a particular fiber. Such spectral calibration may also help when there are physical misalignments between a fiber and its associated set of detector rows.

Figure 3:
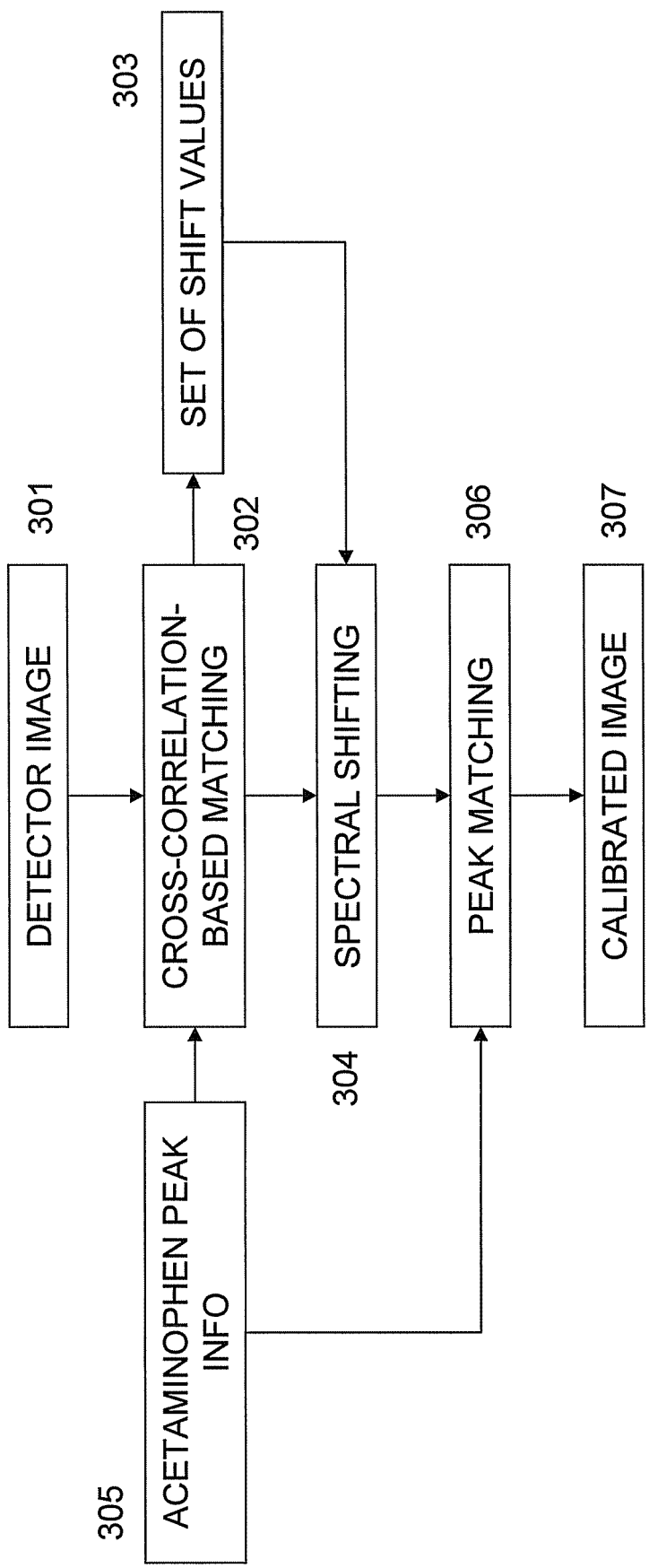
FIG. 3 is a flow chart of a method for spectral calibration according to one embodiment of the disclosure.

FIG. 3 illustrates a broad overview of a spectral calibration method according to one embodiment of the present disclosure. Initially, at block 301 a detector image may be obtained of a known substance, e.g., an acetaminophen sample, using a fiber bundle in a FAST system. It is observed that raw detector data at this stage may look like that shown at the top image in FIG. 11, labeled "Raw Detector Data" 1101. The jagged or misaligned imagery in the raw detector data display may relate to spectral shifts due to non-calibration. Removing these shifts from each fiber (i.e., in fact, each detector row associated with that fiber, because of the super-resolution effect) may be accomplished with a microprocessor and/or in software using an algorithm, such as a correlation-based algorithm (e.g., cross-correlation based matching, as is known in the art), as shown in block 302. Comparing the response of one or more detector rows to that of a calibrated acetaminophen standard, as part of the cross-correlation based matching, allows the one or more detector row's shift value (in pixels) to be determined, as shown in block 303. For example, one detector row may have a shift value of "+1" whereas another detector row may have a shift value of "−4", and so on. As shown in FIG. 3, after computing the shift values, a microprocessor and/or software may act on the raw detector data to remove the shifts, thereby resulting in spectral shifting of the data in the one or more detector rows, as indicated in block 304. The spectral shifting may generate an aligned or calibrated output as shown in the bottom image in FIG. 11, labeled "Calibrated" 1102.

As shown in FIG. 3, after the shifts are removed, a peak-matching algorithm may be applied at block 306 to set the wavelength range of the raw detector data based on information of known acetaminophen peaks in block 305. Once this is completed, a calibrated image may result at block 307. As part of the peak matching algorithm, the acetaminophen standard spectrum may again be applied to each detector row spectrum (now adjusted through spectral shifting) to obtain a wavelength range.

Figure 4:
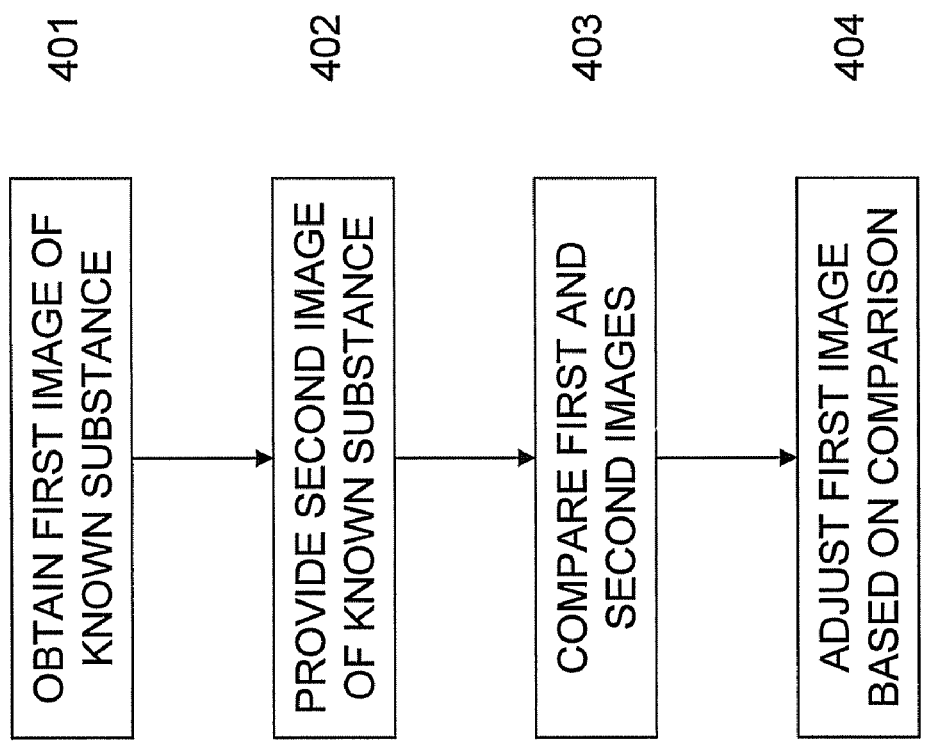
FIG. 4 is a flow chart of a method for spectral calibration according to one embodiment of the disclosure.

With reference now directed towards FIG. 4, another exemplary method for calibrating an image is presented. At block 401 a first image of a known substance is obtained. The first image may typically be obtained by using a FAST system the linear array end of which is at the input of a photon detector. The known substance may be any substance for which a known reference image exists, such as for acetaminophen. At block 402, a second image of the known substance may be provided. The second image may be obtained from an electronic memory device. The first and second images each include at least one pixel and preferably multiple pixels. This second image may be a reference, or library, image which will be used to compare the first image against, as shown in block 403. This comparison may be a correlation algorithm, such as a cross-correlation-based algorithm. At block 404, the first image is adjusted based on the comparison of the first and second images to thereby obtain an adjusted, or calibrated, image. The adjustment may comprise adjusting at least one row of the first image. As discussed above, FIG. 11 shows an exemplary image of raw detector data and calibrated data.

Figure 5:
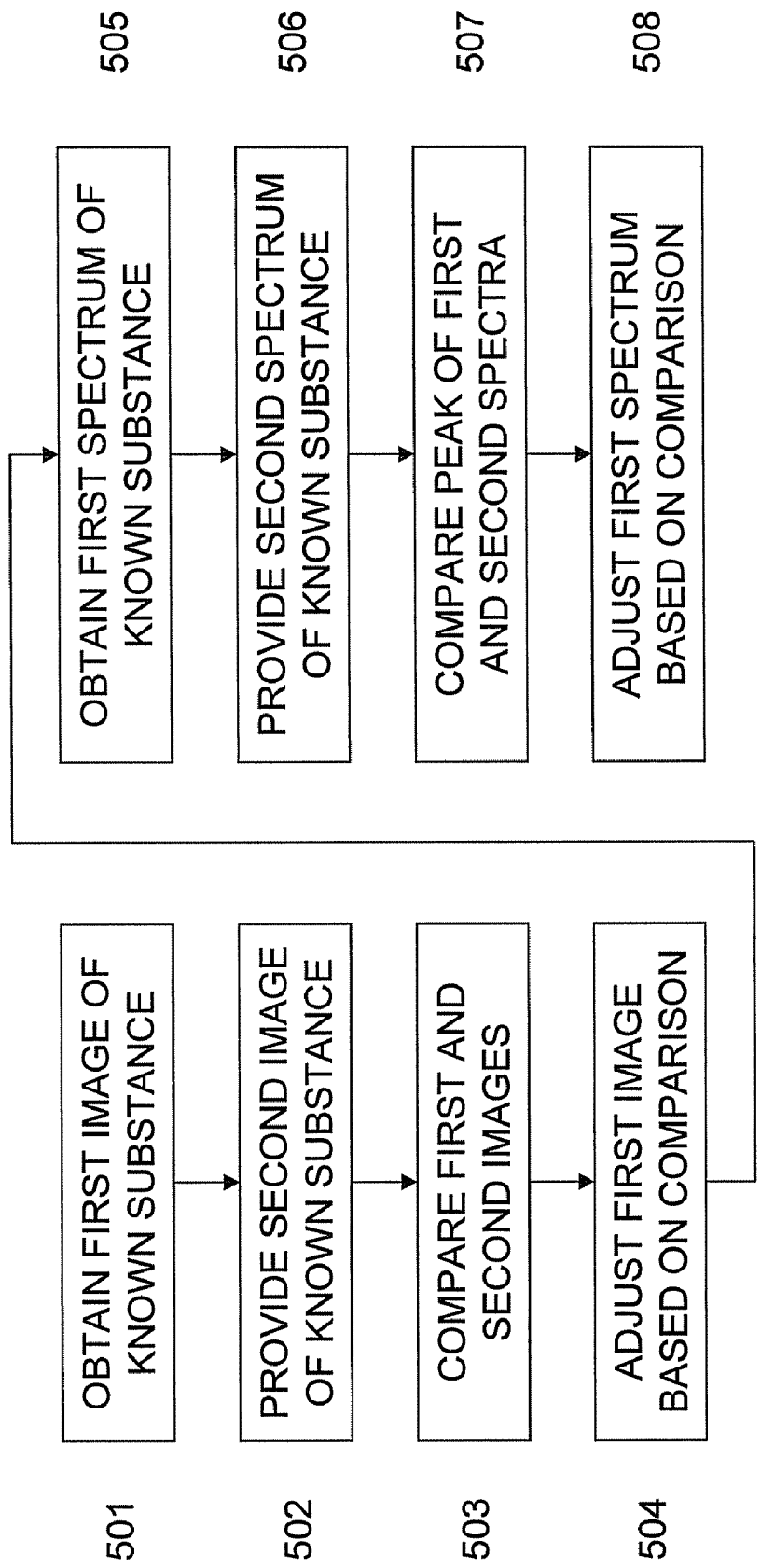
FIG. 5 is a flow chart of a method for spectral calibration according to one embodiment of the disclosure.

FIG. 5 is a further block diagram where blocks 501 through 504 correspond to blocks 401 through 404, respectively, in FIG. 4. After adjusting the first image in block 504, a first spectrum may be obtained of the known substance at block 505. A second spectrum of the known substance may be provided at block 506, where the second spectrum may be a reference, or library, spectrum. Those of skill in the art will readily understand that the first and second spectrum may be obtained at any time and not necessarily after the adjustment of the first image. The first and second spectra preferably each include at least one peak, more preferably the peak in the first and second spectrum correspond to each other. At block 507, a comparison of the first and second spectra is performed and based on that comparison, at block 508 an adjustment is made to the first spectrum.

Figure 6:
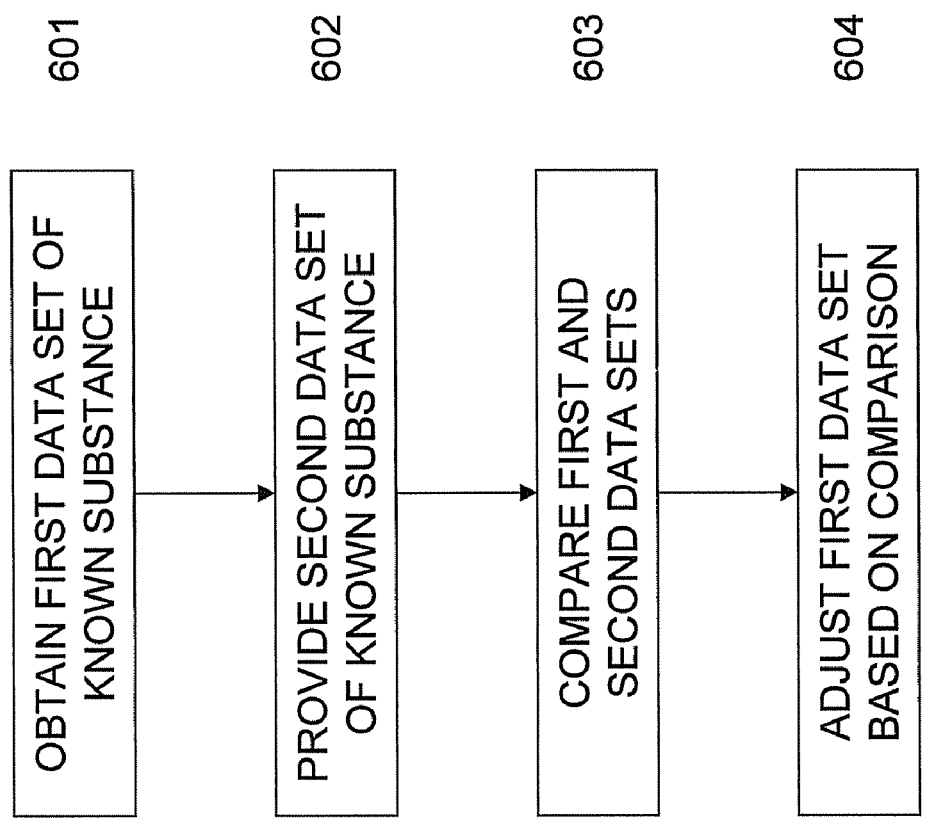
FIG. 6 is a flow chart of a method for spectral calibration according to one embodiment of the disclosure.

With attention now drawn to FIG. 6, another spectral calibration method is depicted. At block 601 a first data set of a known substance is obtained. The first data set may be representative of a first image of a known substance. The first data set may typically be obtained by using a FAST system the linear array end of which is at the input of a photon detector. A microprocessor may be operatively connected to the photon detector for obtaining the first data set. The known substance may be any substance for which a known reference image exists, such as for acetaminophen. At block 602, a second data set of the known substance may be provided. The second data set may be representative of a second image of a known substance. The second data set may be obtained from an electronic memory device operatively connected to the microprocessor. The first and second images each include at least one pixel and preferably multiple pixels. This second data set may be a reference, or library, data set which will be used to compare the first data set against, as shown in block 603. This comparison may be a correlation algorithm, such as a cross-correlation-based algorithm. In block 604, the first data set is adjusted based on the comparison of the first and second data sets to thereby obtain an adjusted, or calibrated, image. The adjustment may comprise adjusting at least one row of the first data set.

Figure 7:
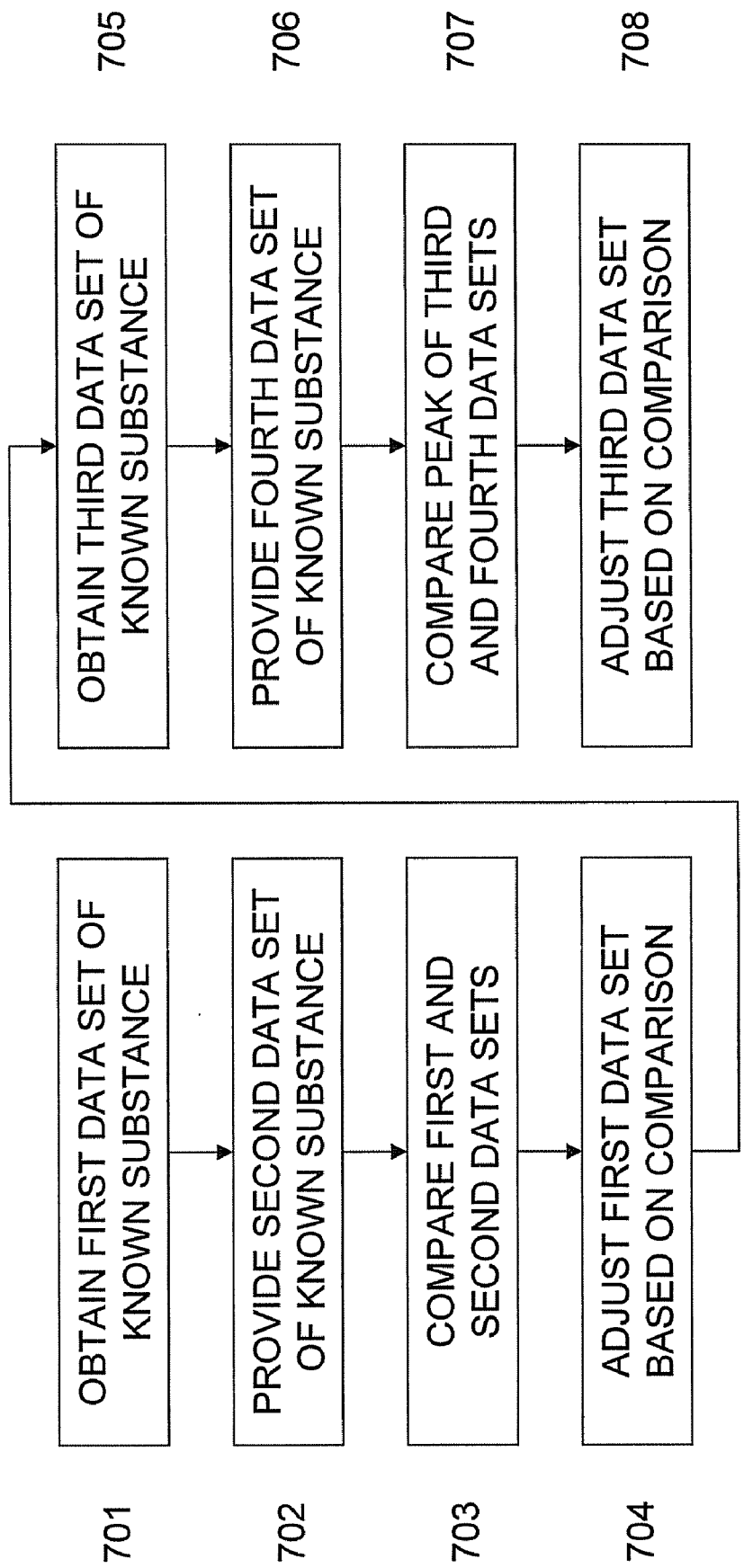
FIG. 7 is a flow chart of a method for spectral calibration according to one embodiment of the disclosure.

FIG. 7 is a further block diagram where blocks 701 through 704 correspond to blocks 601 through 604, respectively, in FIG. 6. After adjusting the first data set in block 704, a third data set may be obtained of the known substance at block 505. The third data set may be representative of a first spectrum of the known substance. A fourth data set may be provided of the known substance at block 706. The fourth data set may be representative of a second spectrum of the known substance, where the second spectrum may be a reference, or library, spectrum. Those of skill in the art will readily understand that the third and fourth data sets may be obtained at any time and not necessarily after the adjustment of the first image at block 704. The first and second spectra preferably each include at least one peak, more preferably the peak in the first and second spectrum correspond to each other. At block 707, a comparison of the third and fourth data sets is performed and based on that comparison, at block 708 an adjustment is made to the third data set.

Figure 8:
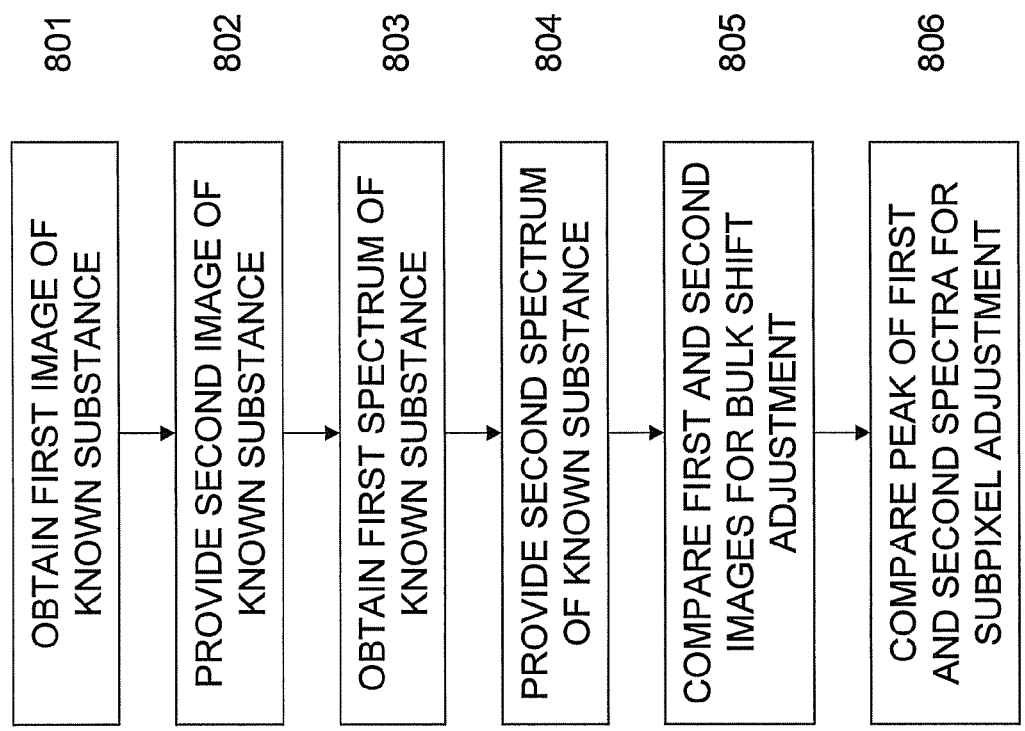
FIG. 8 is a flow chart of a method for spectral calibration according to one embodiment of the disclosure.

FIG. 8 represents yet a further method for spectral calibration. At block 801 a first image of a known substance is obtained. The first image may typically be obtained by using a FAST system the linear array end of which is at the input of a photon detector. The known substance may be any substance for which a known reference image exists, such as for acetaminophen. At block 802, a second image of the known substance may be provided. The second image may be obtained from an electronic memory device. The first and second images each include at least one pixel and preferably multiple pixels. This second image may be a reference, or library, image which will be used to compare the first image against. At block 803 a first spectrum of the known substance is obtained, such as by using a FAST system as described herein. At block 804 a second spectrum of the known substance may be provided, where the second spectrum may be a reference, or library, spectrum. The first and second spectra preferably each include at least one peak, more preferably the peak in the first and second spectrum correspond to each other. At block 805 a comparison of the first and second images is performed to thereby obtain a bulk shift adjustment, i.e., an adjustment of one or more pixels. This comparison may be a correlation algorithm, such as a cross-correlation-based algorithm. At block 806, a comparison of the first and second spectra is performed to thereby obtain a subpixel adjustment, i.e., an adjustment of less than one pixel.

Figure 9:
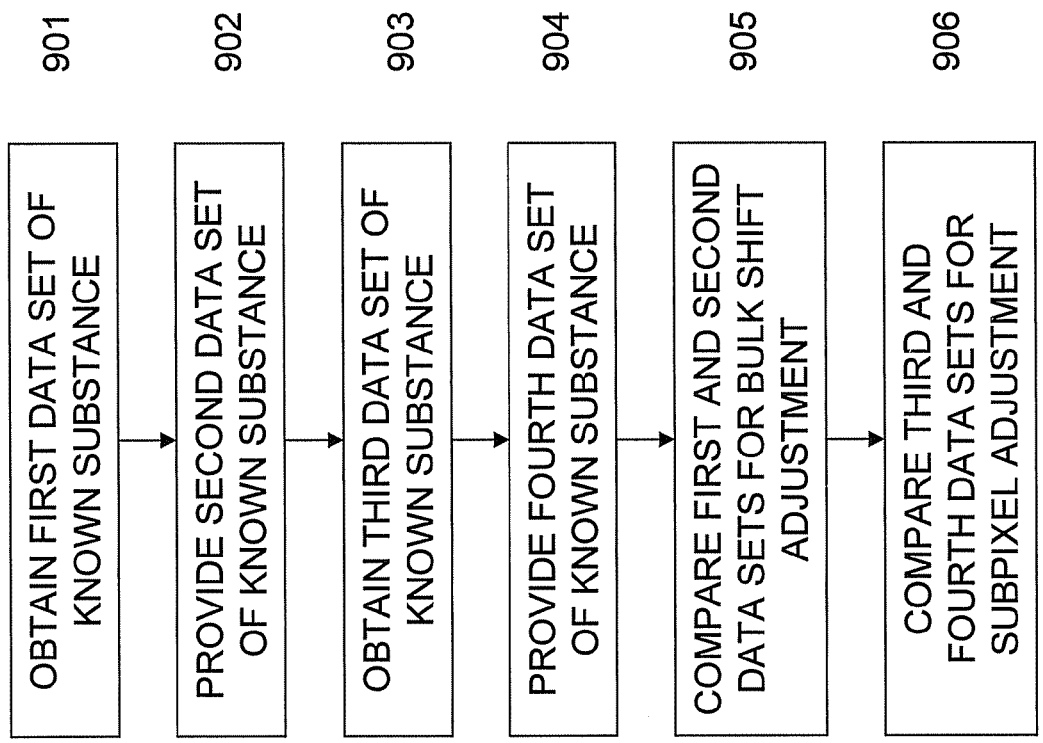
FIG. 9 is a flow chart of a method for spectral calibration according to one embodiment of the disclosure.

Referring now to FIG. 9, still a further method for spectral calibration is presented. At block 901 a first data set of a known substance is obtained, where the first data set may be representative of a first image of the known substance. The first data set may typically be obtained by using a FAST system the linear array end of which is at the input of a photon detector. The known substance may be any substance for which a known reference image exists, such as for acetaminophen. At block 902, a second data set of the known substance may be provided. The second data set may be representative of a second image of the known substance. The second data set may be obtained from an electronic memory device. The first and second data sets each include at least one pixel and preferably multiple pixels. This second data set may be a reference, or library, data set which will be used to compare the first data set against. At block 903 a third data set of the known substance is obtained, such as by using a FAST system as described herein. The third data set may be representative of a first spectrum of the known substance. At block 904 a fourth data set of the known substance may be provided, where the fourth data set may be a reference, or library, data set. The fourth data set may be representative of a second spectrum of the known substance. The third and fourth data sets preferably each include at least one peak, more preferably the peak in the third and fourth data sets correspond to each other. At block 905 a comparison of the first and second data sets is performed to thereby obtain a bulk shift adjustment, i.e., an adjustment of one or more pixels. This comparison may be a correlation algorithm, such as a cross-correlation-based algorithm. At block 906, a comparison of the third and fourth data sets is performed to thereby obtain a subpixel adjustment, i.e., an adjustment of less than one pixel.

Figure 10:
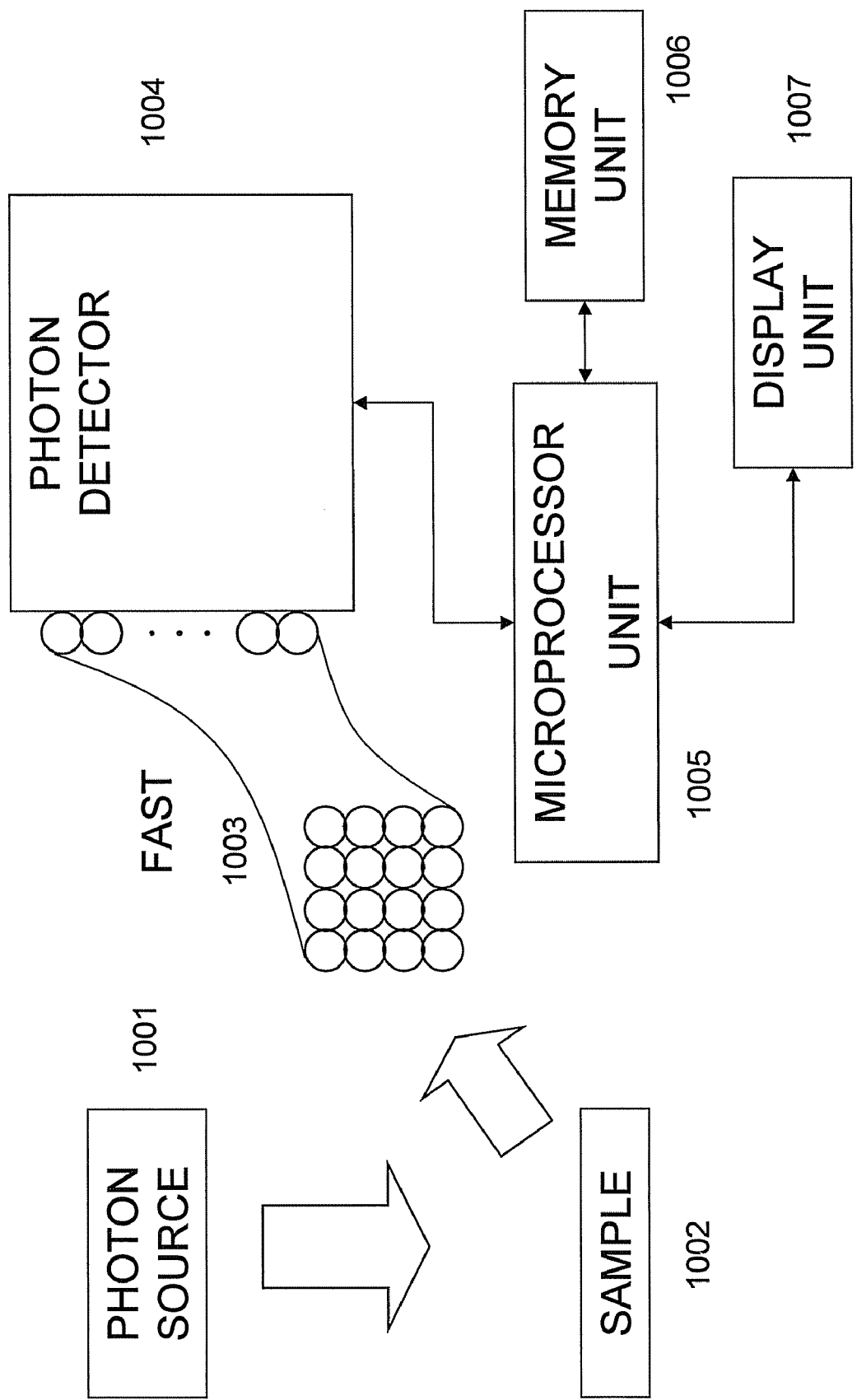
FIG. 10 is a block diagram of a system for spectral calibration according to one embodiment of the disclosure.

FIG. 10 is a block diagram of an exemplary embodiment of a system for performing a spectral calibration as described herein. Those of skill in the art will readily understand that the present disclosure is not limited to the block diagram configuration of FIG. 10. A photon source 1001 provides photons for interacting with the sample 1002 so as to provide photons that enter the two-dimensional array end of the FAST 1003. The photons from the sample may be, for example, emitted by the sample, reflected off of the sample, refracted by the sample, fluoresce from the sample, or scattered by the sample. The scattered photons may be Raman photons. The photons then travel through the FAST system to the linear array end at the input of the photon detector 1004. The photon detector 1004 detects the photons and a microprocessor unit 1005, connected to the photon detector 1004, may receive a signal from the photon detector representative of the detected photons, such as a received data set. The microprocessor unit may also be connected to a memory unit 1006 which may contain a reference, or library, data set of the sample. The microprocessor unit 1005 may obtain from the memory unit 1006 the reference data set and compare the reference data set with the received data set. This comparison may occur in hardware, software, firmware, or some combination thereof. The microprocessor unit may then adjust the received data set based on the comparison of the received and reference data sets to thereby form an adjusted data set. Additionally, a display unit 1007 may be connected to the microprocessor. The display unit 1007 may display an image or images representative of the received data set, the reference data set, the adjusted data set, or combinations thereof.

As discussed above, FIG. 11 is a representation of a raw image 1101 and a calibrated image 1102 of the output of a detector according to an embodiment of the disclosure. Raw detector data may look like that shown at the top image in FIG. 11, labeled "Raw Detector Data" 1101. Spectral shifting may generate an aligned or calibrated output as shown in the bottom image in FIG. 11, labeled "Calibrated" 1102.

Figure 12:
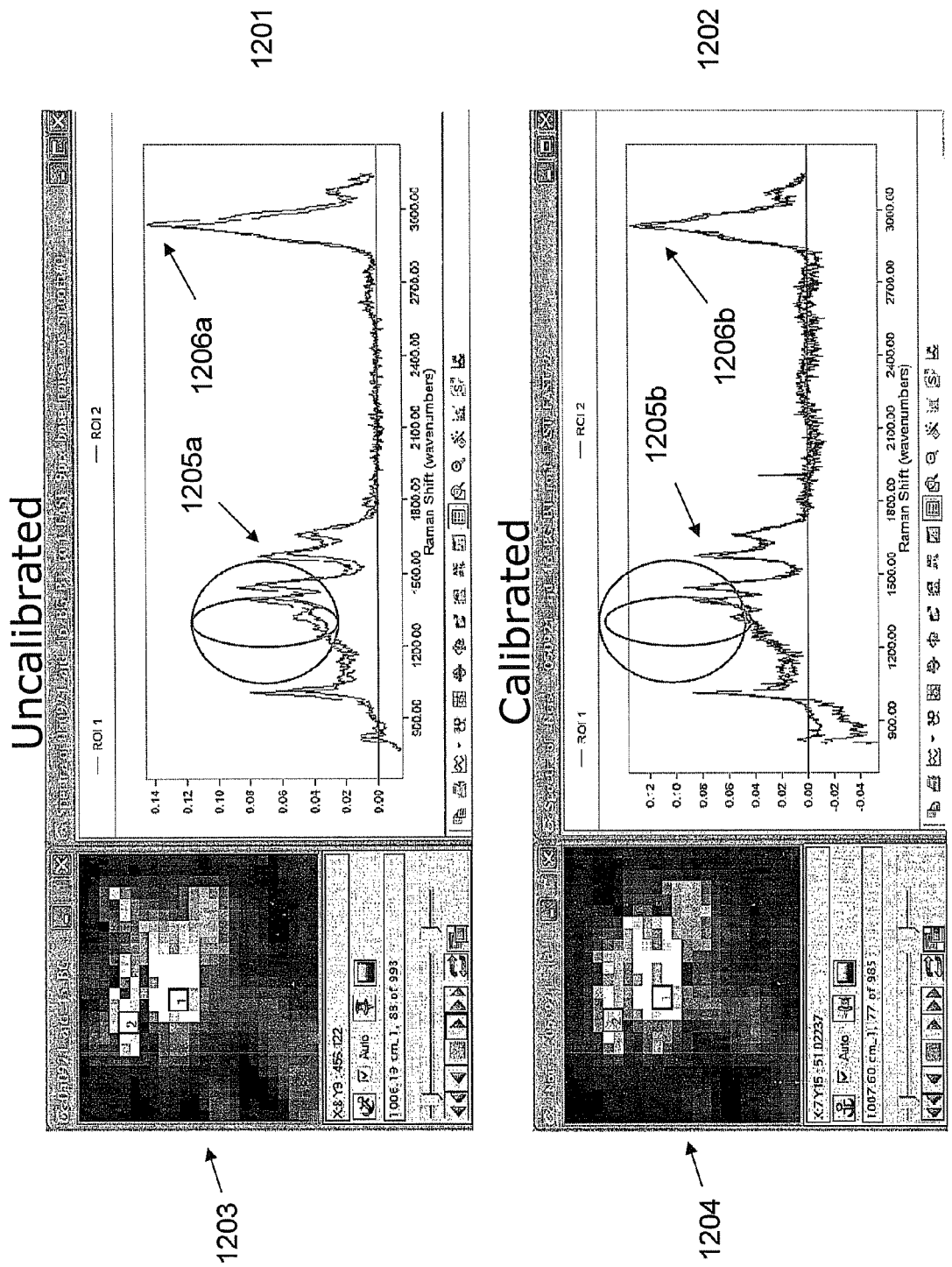
FIG. 12 is a representation of a display output showing an exemplary set of images depicting spectra of two regions of interest in a sample for an uncalibrated condition and a calibrated condition according to an embodiment of the disclosure.

FIG. 12 is a representation of a display output showing an exemplary set of images depicting spectra of two regions of interest in a sample for an uncalibrated condition and a calibrated condition according to an embodiment of the disclosure. For the uncalibrated condition, an image of a sample 1203 indicates a first region of interest 1 and a second region of interest 2. Spectra for these two regions of interest are shown in 1201 where the peaks at 1205*a* and 1206*a* show misalignment. For the calibrated condition, an image of the sample 1204 indicates the first and second regions of interest, 1 and 2, respectively, as above. The spectra for these two regions of interest are shown in 1202 after calibration as described herein. Note that the peaks at 1205*b* and 1206*b* are now aligned. FIG. 12, or parts thereof, may be displayed on a display unit as discussed above in reference to FIG. 11.

Figure 13:
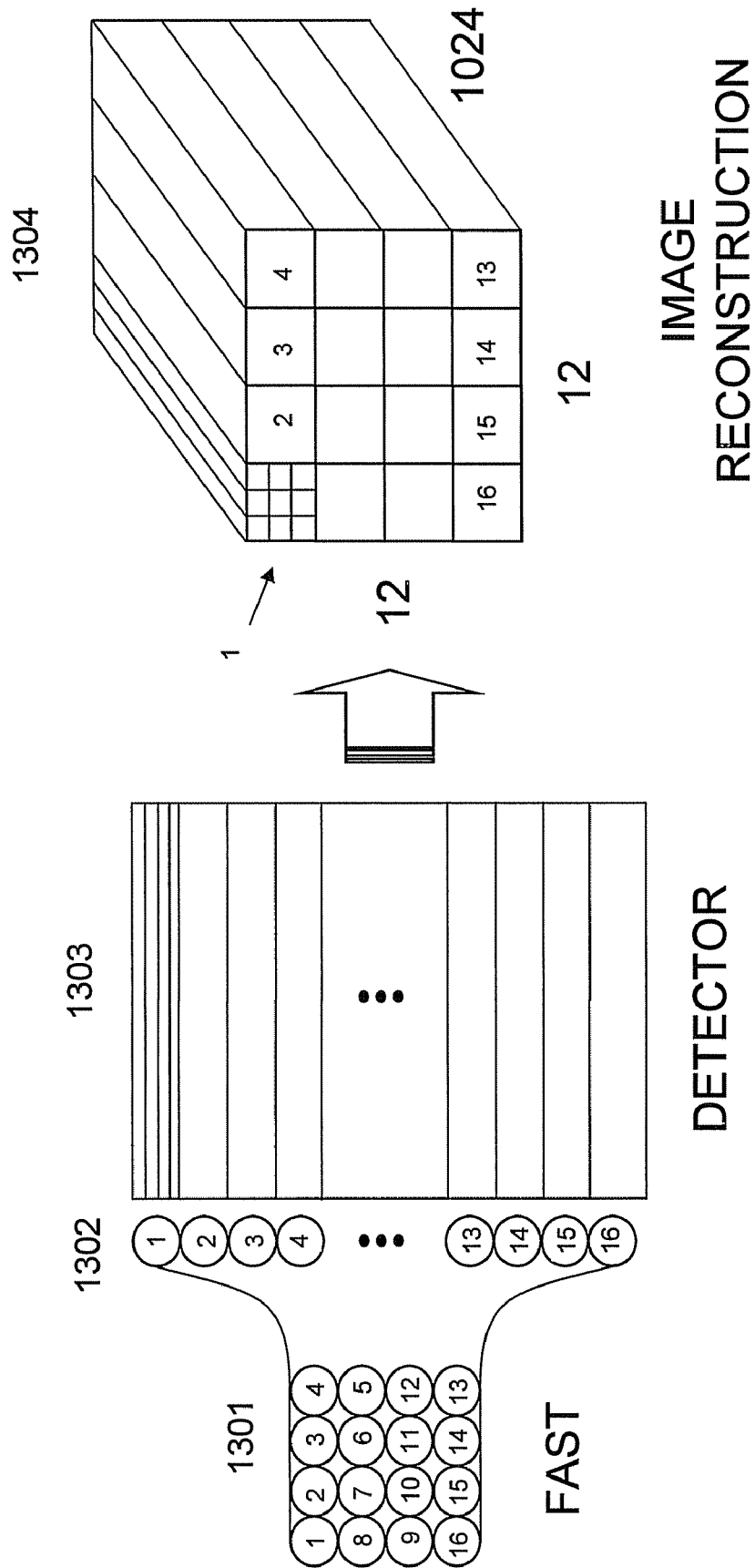
FIG. 13 is a simplified schematic drawing of a FAST system depicting image reconstruction according to an embodiment of the disclosure.

With reference now to FIG. 13, a FAST system is shown with the two-dimensional array end 1301 receiving photons from a sample (not shown for clarity) and the linear array end 1302 providing the photons to the photon detector 1303, where the detector 1303 is shown with multiple rows. With the detector rows properly calibrated (spectrally) and the mapping back to image positions known (i.e., knowledge of mapping of each fiber to its associated set of detector rows through spatial calibration), image reconstruction can be performed according to one embodiment of the present disclosure as discussed herein. Depending on the number of detector rows that each fiber spans, the pixel block 1304 of the reconstructed image is defined. For instance, if each fiber spans 9 detector rows, each fiber may be reconstructed as a 3×3 block of pixels as shown. Without knowledge of the super-resolution spatial mapping with each fiber, a simple raster filling of the 3×3 block may be used.

The overall dimensions of the image may be calculated. For example, if a squarely-packed 4×4 fiber array (i.e., 16 fibers at the imaging end) as shown spans 9×16 detector rows (i.e., nine rows for each of the 16 fibers) on a 1024-width detector (i.e., each detector row having 1024 pixels, as shown), the reconstructed hyperspectral image will be (4*3)× (4*3)×1024=12×12×1024, because the imaging end fiber array size is 4×4 and there is a 3×3 block of detector pixels associated with each fiber in the fiber array. The reconstruction is accomplished for each fiber as follows and as shown in the simplified diagram of FIG. 13. Those of skill in the art will readily understand that the exemplary figures used above are in no way to be interpreted as limiting the disclosure in any way. Assuming that the fibers at the imaging end are in a square configuration as shown in FIG. 13, the data from the nine relevant detector rows for each fiber (in this exemplary embodiment) is read from the calibrated detector array and arranged in a 3×3×1024 block. This block is placed in its corresponding location in the 12×12×1024 image 1304. Each fiber may be reconstructed similarly until the image is built.

High definition and high resolution images, including super-resolution images, can be created by estimating the physical location of fibers relative to the sample and the separation between fibers, and interpolating FAST image pixels accordingly.

Figure 14:
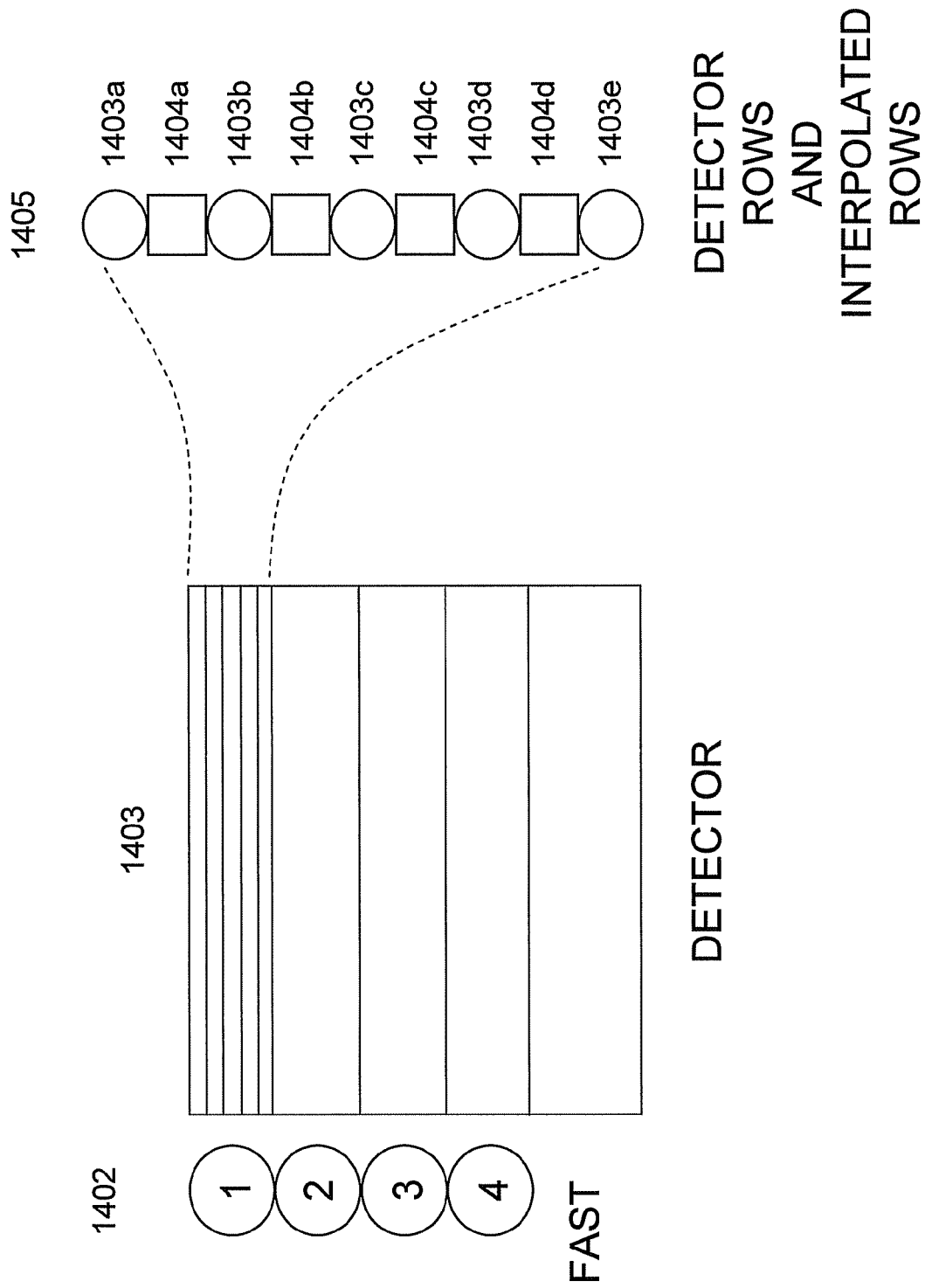
FIG. 14 is a simplified schematic drawing of a FAST system depicting interpolation of detector rows for obtaining a super resolution image according to an embodiment of the disclosure.

FIG. 14 shows an exemplary arrangement of detector rows and interpolated rows according to an embodiment of the disclosure. The linear array end 1402 of a FAST system is shown at the input to a photon detector 1403 having multiple rows. As shown in relation to fiber 1 in the FAST system, multiple detector rows receive the photons from fiber 1. These detector rows are depicted as circles labeled 1403*a* through 1403*e* in the layout 1405. Interpolating between the detector rows results in interpolated rows depicted as squares labeled 1404*a* through 1404*d*. Therefore, the layout 1405 is composed of detector rows 1403*a* through 1403*e* and interpolated rows 1404*a* through 1404*d*. These nine rows may be arranged as shown in FIG. 13 as the nine small boxes comprising block 1 of the image reconstruction block 1304. As will be obvious to those of skill in the art, the present disclosure is not limited to the specific number of fibers, detector rows per fiber, or interpolated rows, as shown in the exemplary embodiment of FIG. 14. Additionally, it will be obvious to those of skill in the art that other fibers in the FAST system may also deliver photons to other multiple detector rows of the photon detector 1403.

Figure 15:
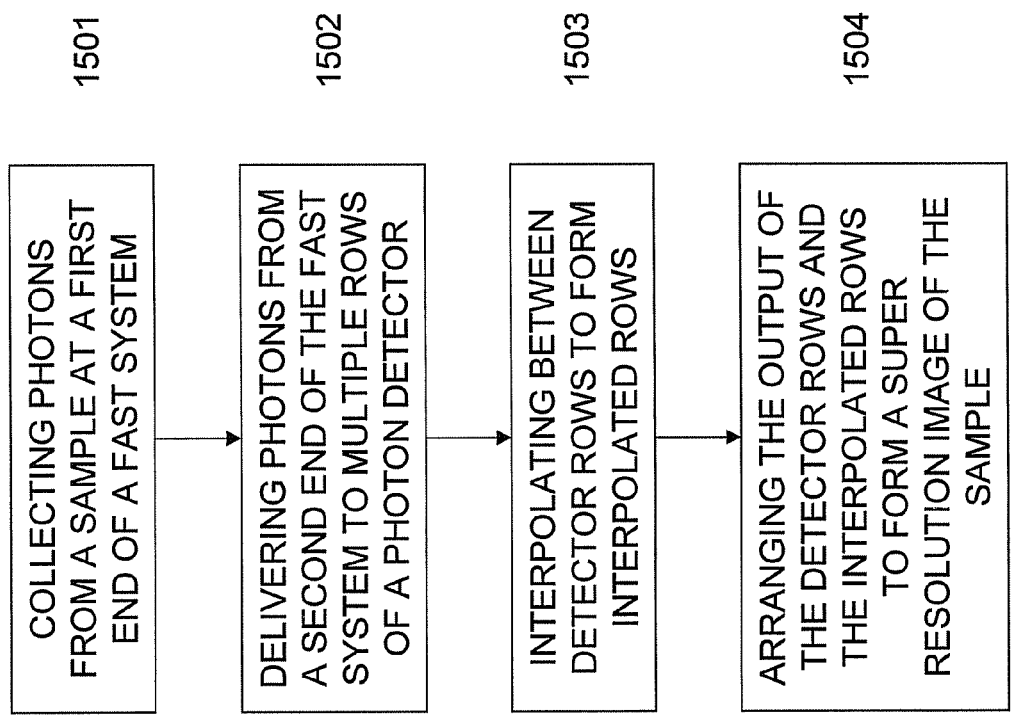
FIG. 15 is a flow chart of a method for obtaining a super resolution image according to an embodiment of the disclosure.

With reference now directed towards FIG. 15, a method for super resolution is depicted in flow chart form. At block 1501, photons from a sample are collected at a first end of a FAST system. At block 1502, photons are delivered from a second end of the FAST system to, for example, multiple detector rows in a photon detector, such as a CCD. These received photons have an associated photon intensity value. At block 1503, an interpolation between detector rows is performed to thereby form interpolated rows. The interpolation may be an average, a weighted average, a mean, or any other similar mathematical operation. The interpolation may be of the photon intensity values of the detector rows and may be limited to only the nearest neighboring detector rows. At block 1504, the output of the detector rows and the interpolated rows are arranged so as to form a super resolution image of the sample.

With reference not directed back to FIG. 10, the system shown may also be used to obtain a super resolution image of the sample 1002. Photons from the sample 1002 are collected the two-dimensional array end of the FAST system 1003. The photons are delivered from the linear array end of the FAST system to, for example, multiple detector rows in the photon detector 1004. These received photons have an associated photon intensity value. The photon detector 1004 detects the photons and a microprocessor unit 1005, connected to the photon detector 1004, may receive a signal from the photon detector representative of the detected photons from the detector rows. The microprocessor unit 1005 may then perform an interpolation, as discussed above, on the detector rows to thereby form interpolated rows. The interpolation may be an average, a weighted average, a mean, or any other similar mathematical operation. The interpolation may be of the photon intensity values of the detector rows and may be limited to only the nearest neighboring detector rows. The interpolation may be accomplished in hardware, software, firmware, or a combination thereof. The microprocessor unit 1005 may arrange the output of the detector rows and the interpolated rows so as to form a super resolution image of the sample 1002. This super resolution image of the sample 1002 may be displayed on the display unit 1007.

The above description is not intended and should not be construed to be limited to the examples given but should be granted the full breadth of protection afforded by the appended claims and equivalents thereto. Although the disclosure is described using illustrative embodiments provided herein, it should be understood that the principles of the disclosure are not limited thereto and may include modification thereto and permutations thereof.

We claim:

1. A method for spectral calibration, comprising:
   obtaining a first image of a known substance using a photon detector and a fiber array spectral translator having plural fibers, wherein said first image comprises at least one pixel;
   providing a second image of said substance wherein said second image comprises at least one pixel;
   comparing said first image with said second image; and
   adjusting at least one pixel of said first image based on said comparison of images to thereby obtain an adjusted image.

2. The method of claim 1 wherein said photon detector is selected from the group consisting of: charge-coupled device ("CCD"), complementary metal oxide semiconductor ("CMOS") detector, and focal plane array sensor.

3. The method of claim 2 wherein said first image comprises at least one row of pixels from said CCD.

4. The method of claim 3 wherein the adjusting comprises adjusting at least one row of said first image.

5. The method of claim 1 wherein the comparing comprises a correlation of said first and second images.

6. The method of claim 1 wherein said second image is a calibrated image of said substance.

7. The method of claim 1 further comprising:
obtaining a first spectrum of said substance from one of said plural fibers wherein said first spectrum comprises at least one peak;
providing a second spectrum of said substance wherein said second spectrum comprises at least one peak;
comparing at least one peak of said first spectrum to at least one peak of said second spectrum; and
adjusting said first spectrum based on said comparison of peaks.

8. The method of claim 7 wherein said second spectrum is a reference spectrum of said substance.

9. A method for spectral calibration, comprising:
obtaining a first data set representative of a first image of a known substance, wherein said first data set is obtained using a photon detector and a fiber array spectral translator having plural fibers;
providing a second data set representative of a second image of said substance;
comparing said first data set with said second data set; and
adjusting said first data set based on said comparison of said first and second data sets.

10. The method of claim 9 wherein said photon detector is selected from the group consisting of: charge-coupled device ("CCD"), complementary metal oxide semiconductor ("CMOS") detector, and focal plane array sensor.

11. The method of claim 10 wherein said first data set comprises at least one row of information from said CCD.

12. The method of claim 11 wherein the adjusting comprises adjusting at least one row information from said CCD.

13. The method of claim 9 wherein the comparing comprises a correlation of said first and second data sets.

14. The method of claim 9 wherein said second data set is representative of a calibrated image of said substance.

15. The method of claim 9 further comprising:
obtaining a third data set representative of a first spectrum of said substance from one of said plural fibers wherein said first spectrum comprises at least one peak;
providing a fourth data set representative of a second spectrum of said substance wherein said second spectrum comprises at least one peak;
comparing a part of said third data set representative of at least one peak of said first spectrum to a part of said fourth data set representative of at least one peak of said second spectrum; and
adjusting said third data set based on said comparison of said third and fourth data sets.

16. The method of claim 15 wherein said fourth data set is representative of a reference spectrum of said substance.

17. A method for spectral calibration, comprising:
obtaining a first image of a known substance using a photon detector and a fiber array spectral translator having plural fibers, wherein said first image comprises at least one pixel;
providing a second image of said substance wherein said second image comprises at least one pixel;
obtaining a first spectrum of said substance from one of said plural fibers wherein said first spectrum comprises at least one peak;
providing a second spectrum of said substance wherein said second spectrum comprises at least one peak;
comparing said first image with said second image to thereby obtain a bulk shift adjustment; and
comparing at least one peak of said first spectrum to at least one peak of said second spectrum to thereby obtain a subpixel adjustment.

18. The method of claim 17 wherein said photon detector is selected from the group consisting of: charge-coupled device ("CCD"), complementary metal oxide semiconductor ("CMOS") detector, and focal plane array sensor.

19. The method of claim 17 wherein the comparing of said first and second images comprises a correlation of said first and second images.

20. The method of claim 17 wherein said second image is a calibrated image of said substance.

21. The method of claim 17 wherein said second spectrum is a reference spectrum of said substance.

22. A method for spectral calibration, comprising:
obtaining a first data set representative of a first image of a known substance using a photon detector and a fiber array spectral translator having plural fibers, wherein said first image comprises at least one pixel;
providing a second data set representative of a second image of said substance, wherein said second image comprises at least one pixel;
obtaining a third data set representative of a first spectrum of said substance from one of said plural fibers wherein said first spectrum comprises at least one peak;
providing a fourth data set representative of a second spectrum of said substance wherein said second spectrum comprises at least one peak;
comparing said first data set with said second data set to thereby obtain a bulk shift adjustment; and
comparing said third data set with said fourth data set to thereby obtain a subpixel adjustment.

23. The method of claim 22 wherein said photon detector is selected from the group consisting of: charge-coupled device ("CCD"), complementary metal oxide semiconductor ("CMOS") detector, and focal plane array sensor.

24. The method of claim 22 wherein the comparing of said first and second data sets comprises a correlation of said first and second data sets.

25. The method of claim 22 wherein said second data set is representative of a calibrated image of said substance.

26. The method of claim 22 wherein said fourth data set is representative of a reference spectrum of said substance.

27. A system for spectral calibration of a known substance, comprising:
a photon source for illuminating said substance with first photons to thereby produce second photons;
a fiber array spectral translator having plural fibers, wherein said fiber array spectral translator receives said second photons;
a photon detector operatively connected to said fiber array spectral translator, wherein said photon detector detects said second photons;
a memory unit comprising a first data set representative of a first image of said substance;
a microprocessor unit operatively connected to said photon detector and said memory unit, wherein said microprocessor obtains a second data set from said second photons, compares said first and second data sets, and adjusts said first data set based on said comparison.

28. The system of claim 27 further comprising a display device operatively connected to said microprocessor unit so as to display an image selected from the group consisting of:

said first image, a second image representative of said second data set, an adjusted image representative of said adjusted first data set, and combinations thereof.

29. The system of claim 27 wherein said photon detector is selected from the group consisting of: charge-coupled device ("CCD"), complementary metal oxide semiconductor ("CMOS") detector, and focal plane array sensor.

30. The system of claim 29 wherein said second image comprises at least one row of pixels from said CCD.

31. The system of claim 30 wherein said microprocessor unit adjusts at least one row of said second image.

32. The system of claim 27 wherein said microprocessor compares said first and second data sets by correlating said first and second data sets.

33. The system of claim 27 wherein said first image is a calibrated image of said substance.

* * * * *